(12) United States Patent
Rázga et al.

(10) Patent No.: US 11,371,038 B2
(45) Date of Patent: Jun. 28, 2022

(54) METHOD FOR ALTERING THE FUNCTIONAL STATE OF MRNA ALLOWING ITS SELECTIVE AND SPECIFIC RECOGNITION

(71) Applicants: Filip Rázga, Senec (SK); Veronika Némethová, Nové Zámky (SK)

(72) Inventors: Filip Rázga, Senec (SK); Veronika Némethová, Nové Zámky (SK)

(73) Assignees: Filip Razga, Senec (SK); Veronika Némethová, Nove Zamky (SK)

(*) Notice: Subject to any disclaimer, the term of this patent is extended or adjusted under 35 U.S.C. 154(b) by 0 days.

(21) Appl. No.: 15/768,586

(22) PCT Filed: Oct. 12, 2016

(86) PCT No.: PCT/SK2016/060002
§ 371 (c)(1),
(2) Date: Apr. 16, 2018

(87) PCT Pub. No.: WO2017/065696
PCT Pub. Date: Apr. 20, 2017

(65) Prior Publication Data
US 2018/0291366 A1    Oct. 11, 2018

(30) Foreign Application Priority Data
Oct. 15, 2015 (SK) .......................... PP 50065-2015

(51) Int. Cl.
*C12N 15/113* (2010.01)
*C12N 15/10* (2006.01)
*C12Q 1/6806* (2018.01)

(52) U.S. Cl.
CPC .......... *C12N 15/102* (2013.01); *C12N 15/113* (2013.01); *C12Q 1/6806* (2013.01); *C12N 2310/113* (2013.01); *C12N 2310/3183* (2013.01); *C12N 2310/331* (2013.01); *C12N 2310/3519* (2013.01)

(58) Field of Classification Search
CPC ............ C12N 15/113; C12N 2310/113; C12N 2310/3183; C12N 2310/3519
See application file for complete search history.

(56) References Cited

U.S. PATENT DOCUMENTS

| | | | | |
|---|---|---|---|---|
| 5,034,506 | A | 7/1991 | Summerton et al. | 528/391 |
| 5,185,444 | A | 9/1993 | Summerton et al. | 544/81 |
| 5,736,327 | A * | 4/1998 | Collins | C12Q 1/6811 |
| | | | | 435/6.12 |
| 6,080,851 | A * | 6/2000 | Pachuk | C12N 15/1135 |
| | | | | 536/24.5 |
| 2001/0010899 | A1* | 8/2001 | Robert | C07H 21/00 |
| | | | | 435/5 |
| 2002/0016008 | A1* | 2/2002 | Lockhart | C12Q 2565/525 |
| | | | | 436/518 |
| 2002/0155496 | A1* | 10/2002 | Charles | C07K 5/06026 |
| | | | | 435/7.1 |
| 2003/0157538 | A1* | 8/2003 | Krull | C12Q 1/6825 |
| | | | | 435/6.12 |
| 2011/0065777 | A1 | 3/2011 | Heidenreich et al. | |
| 2014/0120540 | A1* | 5/2014 | Seligmann | C12Q 1/6827 |
| | | | | 435/6.11 |

FOREIGN PATENT DOCUMENTS

| | | | |
|---|---|---|---|
| EP | 06127100.3 | 12/2006 | |
| JP | H-06-501610 A | 2/1994 | |
| JP | H-08-506724 A | 7/1996 | |
| JP | H-10-509595 A | 9/1998 | |
| JP | 2003-116559 A | 4/2003 | |
| WO | WO-9222303 A1 * | 12/1992 | ............. C07K 14/82 |
| WO | WO-9413793 A1 * | 6/1994 | ......... C12N 15/1135 |
| WO | WO 2004/064782 A2 | 8/2004 | |
| WO | WO 2005/078096 A2 | 8/2005 | |
| WO | WO 2005/11123 8 A2 | 11/2005 | |
| WO | WO 2005/111238 A2 | 11/2005 | |
| WO | WO 2009/023 819 A2 | 2/2009 | |
| WO | WO 2009/023819 A2 | 2/2009 | |
| WO | WO 2011/031520 A1 | 3/2011 | |
| WO | WO 2011/117353 A1 | 9/2011 | |

OTHER PUBLICATIONS

Dinc et al (Plant Physiology, 157:1628-1641, 2011) (Year: 2011).*
Merlo et al (The Plant Cell, 10: 1603-1621, 1998) (Year: 1998).*
Rushdi H. Alul, et al.,"Oxalyl-CPG: a labile support for synthesis of sensitive oligonucleotide derivatives" Nucleic Acids Research, Oxford University Press (1991), vol. 19, No. 7, pp. 1527-1532.
Christen Besanceney-Webler et al.,"Raising the Efficacy of Bioorthogonal Click Reactions for Bioconjugation: A Comparative Study" Angew Chem Int Ed Engl., National Institutes of Health (2012), vol. 50(35), pp. 8051-8056 (12 pages total).

(Continued)

*Primary Examiner* — Richard A Schnizer
(74) *Attorney, Agent, or Firm* — Lee & Hayes, P.C.

(57) ABSTRACT

A method of altering the functional state of any nucleic acid enabling its selective and specific recognition and subsequent selective manipulation and a universal principle for increasing the specificity and selectivity of molecular target recognition at the level of nucleic acids are described. The principle of the specific and selective recognition of nucleic acids is based on simultaneous recognition of two or more sequences of the target nucleic acid, whereas these have to be spaced from each other by a certain defined distance. Such method of nucleic acid recognition through specific recognition of well-defined sequences of the nucleic acid that are spaced from each other by a defined distance, minimizes the probability of stable binding of the interfering construct to inadvertent nucleic acids, thereby dramatically increasing the selectivity of recognition of the targeted nucleic acid. Specific recognition of defined sequences of a nucleic acid localized at a certain defined distance from each other is achieved by simultaneous complementary interference of short sequence-specific oligonucleotides being mutually interconnected by size-specific linking moiety.

35 Claims, 1 Drawing Sheet

Specification includes a Sequence Listing.

(56) References Cited

OTHER PUBLICATIONS

Charles E. Hoyle et al.,"Thiol-Ene Click Chemistry", Angew. Chem Int. Ed. (2010), vol. 49, pp. 1540-1573.
John C. Burnett et al.,"RNA-Based Therapeutics: Current Progress and Future Prospects", Chemistry & Biology, Elsevier Ltd. (2012), vol. 19, pp. 60-71.
University Department of Haematology, Royal Liverpool University Hospital "Antisense therapeutics in chronic myeloid leukaemia: the promise, the progress and the problems" Leukemia, Macmillan Publishers Ltd. (2000), vol. 14, pp. 347-355.
Christofer Diakos et al.,"RNAi-mediated silencing of TEL/AML1 reveals a heat-shock protein-and survivin-dependent mechanism for survival" BLOOD, www.bloodjournal.org, (2007), vol. 109, No. 6, pp. 2607-2610 (5 pages total).
Nathalie Dias et al.,"Antisense Oligonucleotides: Basic Concepts and Mechanisms" Mol Cancer Ther, American Association for Cancer Research (2002), vol. 1 pp. 347-355.
John C. Chaput et al.,"TNA Synthesis by DNA Polymerases" J. Am. Chem. Soc. (2003), vol. 125, pp. 9274-9275.
Nicholas J. Greco et al., "Synthesis and site-specific incorporation of a simple fluorescent pyrimidine" Nature Protocols (2007), vol. 2, No. 2, pp. 305-316.
Wei Guo et al., "Small interfering RNA-based molecular therapy of cancers" Chinese Journal of Cancer (2013) DOI: 10.5732/cjc.012. 10280, (14 pages total).
Burkhard Jansen et al., "Antisense therapy for cancer—the time of truth", The Lancet Oncology (2002), vol. 3, pp. 672-683.
Andres Jäschke et al., "Synthesis and properties of oligodeoxyribonucleotide-polyethylene glycol conjugates", Nucleic Acids Research, Oxford University Press (1994) vol. 22, No. 22, pp. 4810-4817.
Veeran Gowda Kadajji et al., "Water Soluble Polymers for Pharmaceutical Applications", Polymers (2011), vol. 3, pp. 1972-2009.
Alexei A. Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron, Elsevier Science Ltd. (1998), vol. 54, pp. 3607-3630.
Muthiah Manoharan et al., "Allyl Group as a Protecting Group for Internucleotide Phosphate and Thiophosphate Linkages in Oligonucleotide Synthesis: Facile Oxidation and Deprotection Conditions", Organic Letters, American Chemical Society (2000), vol. 2, No. 3, pp. 243-246.
Krzysztof Matyjaszewski et al., "Atom Transfer Radical Polymerization", Chem. Rev., American Chemical Society (2001), vol. 101, pp. 2921-2990.
Peter E. Nielsen et al., "Sequence-Selective Recognition of DNA by Strand Displacement with a Thymine-Substituted Polyamide", Reports, (1991), pp. 1497-1500.
Satoshi Obika et al., "Synthesis of 2'-O, 4'-C-Methyleneuridine and -cytidine. Novel Bicyclic Nucleosides Having a Fixed $C_3$ -endo Sugar Puckering", Tetrahedron Letters, Elsevier Science, Ltd. (1997), vol. 38, No. 50, pp. 8735-8738.
Kathleen F. Pirollo et al., "Antisense therapeutics: from theory to clinical practice", Pharmacology &Therapeutics, Elsevier Science Inc. (2003), vol. 99, pp. 55-77.
Stanislav et al., "Copper-Catalyzed Azide-Alkyne Click Chemistry for Bioconjugation", National Institutes of Health, Curr Protoc Chem Biol. (2011) vol. 3(4), pp. 153-162 (14 pages total).
J. Rangatia et al., "Transient or long-term silencing of BCR-ABL alone induces cell cycle and proliferation arrest, apoptosis and differentiation" Leukemia, Nature Publishing Group (2006) vol. 20, pp. 68-76.
Valentina Rapozzi et al., "Antisense locked nucleic acids efficiently suppress BCR/ABL and induce cell growth decline and apoptosis in leukemic cells", Mol Cancer Ther (2006) vol. 5, pp. 1683-1692.
Michaela Scherr et al., "Specific inhibition of bcr-abl gene expression by small interfering RNA", Blood, American Society of Hematology (2003), ISSN 1528-0020, vol. 101, pp. 1566-1569.

M. Scherr et al., "Stable RNA Interference (RNAi) as an option for anti-bcr-abl therapy", Gene Therapy, Nature Publishing Group (2005), vol. 12, pp. 12-21.
Rolf A. Stahel et al., "Antisense oligonucleotides for cancer therapy—an overview" Elsevier Science Ireland Ltd., Lung Cancer (2003), vol. 41, pp. 581-588.
James Summerton et al., "Morpholino Antisense Oligomers: Design, Preparation, and Properties", Antisense & Nucleic Acid Drug Development (1997), vol. 7, pp. 187-195.
James E. Summerton, "Morpholino, siRNA, and S-DNA Compared: Impact of Structure and Mechanism of Action on Off-Target Effects and Sequence Specificity", Current Topics in Medical Chemistry, Bentham Science Publishers Ltd. (2007), vol. 7, pp. 651-660.
Kazuhiro Tanaka et al., "EWS-Fli1 Antisense Oligodeoxynucleotide Inhibits Proliferation of Human Ewing's Sarcoma and Primitive Neuroectodermal Tumor Cells", Antisense Growth Inhibition of Ewing's Sarcoma and Related Tumors, The American Society for Clinical Investigation, Inc. (1997), vol. 99, No. 2, pp. 239-247.
Nasuo Ueda et al., "Synthesis of N-(2,3-Dihydroxypropyl) Derivatives of Nucleic Bases", Faculty of Engineering, Osaka University (1971), vol. 8, pp. 827-829.
Akshay K. Vaishnaw et al., "A status report on RNAi therapeutics", Silence, A Journal of RNA regulation (2010), vol. 1, No. 14, pp. (13 pages total).
Laixin Wang et al., "Progress in the Delviery of Therapeutic Oligonucleotides: Organ/Cellular Distribution and Targeted Delivery of Oligonucleotides In Vivo", Antisense and Nucleic Acid Drug Development (2003), vol. 13, pp. 169-189.
Xia Wei, "Coupling activators for the oligonucleotide synthesis via phosphoramidite approach", Tetrahedron, Elsevier Ltd. (2013), vol. 69, pp. 3615-3637.
International Search Report dated Jun. 6, 2017 in corresponding PCT International Application No. PCT/SK2016/060002.
Written Opinion dated Jun. 6, 2017 in corresponding PCT International Application No. PCT/SK2016/060002.
R.R. Subramanian et al., "Enhancing antisense efficacy with multimers and multi-targeting oligonucleotides (MTOs) using cleavable linkers," Nucleic Acids Research, vol. 43, No. 19, pp. 9123-9132, Oct. 7, 2015.
Australian office action dated Nov. 14, 2019 in Australian application No. 2016336851, a foreign corresponding application of U.S. Appl. No. 15/768,586, 4 pp.
Gumbiner-Russo, "Physical Analyses of *E.coli* Heteroduplex Recombination Products In Vivo: On the Prevalence of 5' and 3' Patches," 2007. PLOS One, 2(11): e1242. 15 pp.
Hanin, "Practical methods of prolonging life beyond the species limit: verification of the proposed theory of gerontogenesis. The problem of practical human immortality." 2004. Translated. Available at http://www.moscowuniversityclub.ru/home.asp?artId= 13579, 7 pp.
Translated Russian office action daed Aug. 26, 2019 in Russian application No. 2018117650/04(027523), a foreign corresponding application of U.S. Appl. No. 15/768,586, 15 pp.
Subramanian et al., "Enhancing antisense efficacy with multiimers and multi-targeting oligonucleotides (MTOs) using cleavable linkers," Oct. 2015. Nucleic Acids Research, 43(19): 9123-9132.
Australian office action dated Mar. 12, 2020 in Australian application No. 2016336851, a foreign corresponding application to U.S. Appl. No. 15/768,586, 3 pages.
European office action dated Feb. 23, 2021 in European application No. 1684534838, a foreign corresponding application to U.S. Appl. No. 15/768,586, 9 pages.
European office action dated Sep. 3, 2020 in European application No. 16845348.8, a foreign corresponding application to U.S. Appl. No. 15/768,586, 7 pages.
Japanese office action dated Jul. 1, 2020 in Japanese application No. 2018-539222, a foreign corresponding application to U.S. Appl. No. 15/768,586, 10 pages.
Korean office action dated Nov. 30, 2020 in Korean application No. 10-2018-7010701, a foreign corresponding application to U.S. Appl. No. 15/768,586, 5 pages.

(56) References Cited

OTHER PUBLICATIONS

Korean office action dated Apr. 27, 2020 in Korean application No. 10-2018-7010701, a foreign corresponding application to U.S. Appl. No. 15/768,586, 9 pages.
Mew Zealand office action dated Mar. 11, 2021 in New Zealand application No. 742493, a foreign corresponding application to U.S. Appl. No. 15/768,586, 5 pages.

* cited by examiner

SEQUENCE LISTING

```
<160> NUMBER OF SEQ ID NOS: 26

<210> SEQ ID NO 1
<211> LENGTH: 357
<212> TYPE: RNA
<213> ORGANISM: Homo sapiens

<400> SEQUENCE: 1
acguuccuga ucuccucuga cuaugagcgu gcagagugga gggagaacau ccgggagcag       60
cagaagaagu guuucagaag cuucucccug acauccgugg agcugcagau gcugaccaac      120
ucguguguga aauccagac uguccacagc auuccgcuga ccaucaauaa ggaagaagcc      180
cuucagcggc caguagcauc ugacuuugag ccucaggguc ugagugaagc cgcucguugg      240
aacuccaagg aaaaccuucu cgcuggaccc agugaaaaug accccaaccu uuucguugca      300
cuguaugauu uuguggccag uggagauaac acucuaagca uaacuaaagg ugaaaag         357
```

```
<210> SEQ ID NO 2
<211> LENGTH: 237
<212> TYPE: RNA
<213> ORGANISM: Homo sapiens

<400> SEQUENCE: 2
aucaaaauca caguggaugg gccccgagaa ccucgaaauc guacugagaa gcacuccaca    60
augccagacu caccugugga ugugaagacg caaucuaggc ugacuccucc aacaaugcca   120 ccuccccccaa cuacucaagg agcuccaaga accaguucau uuacaccgac aacguuaacu  180
aauggcacga gccauucucc uacagccuug aauggcgccc ccucaccacc caauggc      237

<210> SEQ ID NO 3
<211> LENGTH: 149
<212> TYPE: RNA
<213> ORGANISM: Homo sapiens

<400> SEQUENCE: 3
uuugaagaua gagacaggouc ucaucgggag gaaauggaga augaaguuga gagcgucaca   60
gggaugcuua acgaggccga ggggaaggcc auuaagcugg ccaaggacgu ggcgucccuc  120
aguucccagc uccaggacac ccaggaguu                                    149

<210> SEQ ID NO 4
<211> LENGTH: 297
<212> TYPE: RNA
<213> ORGANISM: Homo sapiens

<400> SEQUENCE: 4
ucccuguggg gggcaacaaa gacaaggaaa acaccggggu ccuucaugcc uucccaccuu   60
gugaguucuc ccagcaguuc cuggauuccc cugccaaggc acuggccaaa ucugaagaag  120
auuaccuggu caugaucauu guccgugcuu ugaaaagucc agccgcauuu caugagcaga  180
gaaggagcuu ggagcgggcc aggacagagg acuaucucaa acggaagauu cguuccggc   240 cggagagauc ggagcugguc aggaugcaca uuuuggaaga gaccucggcu gagccau     297

<210> SEQ ID NO 5
<211> LENGTH: 297
<212> TYPE: RNA
<213> ORGANISM: Homo sapiens

<400> SEQUENCE: 5
aaaugaacuu uucccuagag aauacuuccg ucguuugucu ucgcaggaug uacucaggug   60
ucaguccucu ucuaagagga agucuaaaga ugaagaagaa gaugaagagu cagaugaugc  120
ugaugauggg aauaacuggg aacacaaguc cauuuggaca gcccuuuagu caagcuggag  180
ggcagccaau gggagccacu ggagugaacc cccaguuagc cagcaaacag agcauggucaa 240 acaguuugcc caccuucccu acagauauca agaauacuuc agucaccaac gugccaa    297

<210> SEQ ID NO 6
<211> LENGTH: 237
<212> TYPE: RNA
<213> ORGANISM: Homo sapiens

<400> SEQUENCE: 6
uuaugaucag cagcaugauu ccuauaguca aaaccagcag uccuaucauu cacaaaggga   60
aaacuacagc caccacacac aagauaugcc cugcguccaa gcccauauaa gcccuucccc  120
uccagguucc aguuaugcgg cgcagacaua cagcucggaa uacaccacgg agaucaugaa  180
```

```
cccgacuac accaagcuga ccauggaccu uggcagcacu gagaucacgg cuacagc      237
```

<210> SEQ ID NO 7
<211> LENGTH: 297
<212> TYPE: RNA
<213> ORGANISM: Homo sapiens

<400> SEQUENCE: 7

```
gagcgcuaug ucaccuccug uuugcggaag aaaaggaaac cucaagcuga gaaaguugau   60
gugauugccg gcuccuccaa gaugaagggc uucucguccu cagagucgga gagcuccagu  120
gaguccagcu ccucugacag cgaagacucc gaaacagcau cugcauugcc gggaccggau  180
augagcauga aaccuagugc cgcccugucu ccaucccug cacuucccuu ucucccacca   240
acuucugacc caccagacca cccacccagg gagccaccuc cacagcccau caugccu     297
```

<210> SEQ ID NO 8
<211> LENGTH: 17
<212> TYPE: DNA
<213> ORGANISM: Artificial Sequence
<220> FEATURE:
<223> OTHER INFORMATION: Oligonucleotide

<400> SEQUENCE: 8

```
cttccttatt gatggtc                                                 17
```

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide

<400> SEQUENCE: 9

```
gatgctactg gccgctg                                                 17
```

<210> SEQ ID NO 10
<211> LENGTH: 16
<212> TYPE: DNA
<213> ORGANISM: Artificial Sequence
<220> FEATURE:
<223> OTHER INFORMATION: Oligonucleotide

<400> SEQUENCE: 10

```
gcccatccac tgtgat                                                  16
```

<210> SEQ ID NO 11
<211> LENGTH: 18
<212> TYPE: DNA
<213> ORGANISM: Artificial Sequence
<220> FEATURE:
<223> OTHER INFORMATION: Oligonucleotide

<400> SEQUENCE: 11

```
ggagtgcttc tcagtacg                                                18
```

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12

```
ccgatgagac ctgtctctat                                              20

<210> SEQ ID NO 13
<211> LENGTH: 15
<212> TYPE: DNA
<213> ORGANISM: Artificial Sequence
<220> FEATURE:
<223> OTHER INFORMATION: Oligonucleotide

<400> SEQUENCE: 13
gctctcaact tcatt                                                   15

<210> SEQ ID NO 14
<211> LENGTH: 14
<212> TYPE: DNA
<213> ORGANISM: Artificial Sequence
<220> FEATURE:
<223> OTHER INFORMATION: Oligonucleotide

<400> SEQUENCE: 14
tcttcagatt tggc                                                    14

<210> SEQ ID NO 15
<211> LENGTH: 17
<212> TYPE: DNA
<213> ORGANISM: Artificial Sequence
<220> FEATURE:
<223> OTHER INFORMATION: Oligonucleotide

<400> SEQUENCE: 15
gacaatgatc atgacca                                                 17

<210> SEQ ID NO 16
<211> LENGTH: 16
<212> TYPE: DNA
<213> ORGANISM: Artificial Sequence
<220> FEATURE:
<223> OTHER INFORMATION: Oligonucleotide

<400> SEQUENCE: 16
gaaatgcggc tggact                                                  16

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide

<400> SEQUENCE: 17
catcatctga ctcttcat                                                18

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide

<400> SEQUENCE: 18
atggacttgt gttcccagt                                               19

<210> SEQ ID NO 19
<211> LENGTH: 15
<212> TYPE: DNA
<213> ORGANISM: Artificial Sequence
```

```
<220> FEATURE:
<223> OTHER INFORMATION: Oligonucleotide

<400> SEQUENCE: 19
cctccagctt gacta                                                    15

<210> SEQ ID NO 20
<211> LENGTH: 16
<212> TYPE: DNA
<213> ORGANISM: Artificial Sequence
<220> FEATURE:
<223> OTHER INFORMATION: Oligonucleotide

<400> SEQUENCE: 20
cttgtgtgtg gtggct                                                   16

<210> SEQ ID NO 21
<211> LENGTH: 17
<212> TYPE: DNA
<213> ORGANISM: Artificial Sequence
<220> FEATURE:
<223> OTHER INFORMATION: Oligonucleotide

<400> SEQUENCE: 21
atattgggct tggacgc                                                  17

<210> SEQ ID NO 22
<211> LENGTH: 16
<212> TYPE: DNA
<213> ORGANISM: Artificial Sequence
<220> FEATURE:
<223> OTHER INFORMATION: Oligonucleotide

<400> SEQUENCE: 22
gcataactgg aacctg                                                   16

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide

<400> SEQUENCE: 23
tggactcact ggagctct                                                 18

<210> SEQ ID NO 24
<211> LENGTH: 18
<212> TYPE: DNA
<213> ORGANISM: Artificial Sequence
<220> FEATURE:
<223> OTHER INFORMATION: Oligonucleotide

<400> SEQUENCE: 24
tcggagtctt cgctgtca                                                 18

<210> SEQ ID NO 25
<211> LENGTH: 18
<212> TYPE: DNA
<213> ORGANISM: Artificial Sequence
<220> FEATURE:
<223> OTHER INFORMATION: Oligonucleotide

<400> SEQUENCE: 25
cggtcccggc aatgcaga                                                 18
```

```
<210> SEQ ID NO 26
<211> LENGTH: 18
<212> TYPE: DNA
<213> ORGANISM: Artificial Sequence
<220> FEATURE:
<223> OTHER INFORMATION: Oligonucleotide

<400> SEQUENCE: 26
gcggcactag gtttcatg                                                 18
```

METHOD FOR ALTERING THE FUNCTIONAL STATE OF MRNA ALLOWING ITS SELECTIVE AND SPECIFIC RECOGNITION

CROSS-REFERENCE TO RELATED APPLICATIONS

The present application is a 35 U.S.C. §§ 371 national phase conversion of PCT/SK2016/060002, filed Oct. 12, 2016, which claims priority to Slovakia Patent Application No. PP 50065-2015, filed Oct. 15, 2015, the contents of which are incorporated herein by reference. The PCT International Application was published in the English language.

FIELD OF THE INVENTION

The invention relates to alteration of the functional state of any nucleic acid enabling its specific and selective recognition and subsequent selective manipulation. The present solution is fully universal and accessible in fields such as biotechnology, molecular biology, virology, medicine, etc. The invention has direct applicability and broad therapeutic potential most preferably in the field of oncology, but it is not restricted to this particular area.

BACKGROUND OF THE INVENTION

In the view of the current state of the art, unlike other, chemically similar constructs, the solution described in the present invention is designed with a diametrically different objective.

The bivalent system described in document WO 2011/117353 (Moeller, Udesen, 2011) represents a multifunctional construct for simultaneous interaction of the linked oligonucleotides with two separate target nucleic acids in order to saturate their binding sites and modulate thus their biological function. Since each oligonucleotide recognizes different target nucleic acid molecule, the construct itself principally functions in the same way as standard antisense oligonucleotide (with respect to the individual target nucleic acid molecules) and by no means increases the selectivity of their recognition.

Analogously, the conjugate of antisense oligonucleotides described in document WO 2011/031520 (Agrawal et al., 2011) is designed to recognize two nucleic acid molecules (either identical or different), while similarly to document WO 2011/117353 (Moeller, Udesen, 2011), recognizes the target nucleic acid molecules individually (i.e., via a single antisense oligonucleotide). Hence the document does not address the issue of their selective recognition.

Other chemically similar constructs described in documents WO 2009/023819 (Kandimalla et al., 2009), WO 2005/111238 (Epstein et al., 2005), WO 2005/078096 (Zamore et al., 2005), WO 2004/064782 (Agrawal et al., 2004) were designed for immunoregulation, to enhance their cellular uptake, miRNA recruiting and immunostimulatory purposes, respectively. However, none of them solves the problem of selective recognition of target nucleic acid molecules.

In all these cases, the described constructs represent only a kind of "superior", multivalent form of the interacting molecule, moreover that is designed to solve diametrically different issue, which is unrelated to the present solution. The fundamental differences thus lie in the fact that while the existing constructs do not solve the promiscuity of antisense oligonucleotides, the present invention provides a solution to this problem.

While the current scientific knowledges in this field are directed to a treatment of oncological diseases it is important to note that fusion genes characteristic exclusively to tumor cells are causal in many tumor disease (leukemias, lymphomas, sarcomas, etc.) and can be certainly considered as a prospective target for anticancer therapy. The unique sequence of fusion nucleic acid allows for specific and selective targeting of tumor cells without therapeutic intervention in healthy cells. Anticancer therapies based on the interference of therapeutic agents with nucleic acids thus can be directed against causal fusion nucleic acids and thus to achieve therapeutic effect exclusively in tumor cells. In the context of antisense strategies it means targeted silencing of fusion genes via interference with the fusion mRNA, thereby preventing the synthesis of causal fusion proteins.

The issue of insufficient specificity of these antisense strategies (in the terms of binding specificity of therapeutic agents to the target sequence of mRNA, their binding affinity to the target mRNA and binding energy with the target mRNA) has been solved primarily by chemical modifications of the therapeutic agents, e.g. by chemical modification of ribose and/or phosphodiester backbone (Pirollo, Rait et al., 2003; Stahel, Zangmeister-Wittke, 2003; Jansen, Zangemeister-Wittke, 2002). Despite this, a final solution has not yet been identified, since modified therapeutic agents are not sufficiently specific and selective, and they cause silencing of therapeutically off-target genes (Burnett, Rossi, 2012). This consequently influences the expression of non-targeted proteins resulting in serious clinical side effects with negative impact on patient quality of life.

With respect to the principle of target mRNA recognition, the application of a single therapeutic, sequence-specific oligonucleotide which binds to a specific region of the target mRNA represents a commonly used standard of antisense strategies. In case of fusion mRNA this specific region is most commonly the site of the direct fusion of the two individual fusion partners (Diakos et al., 2007; Rangatia, Bonnet, 2006; Rapozzi et al., 2006; Scherr et al., 2005; Scherr et al., 2003; Tanaka et al., 1997). The published data however clearly indicate to the fact that despite a significant improvement in the physico-chemical properties of antisense therapeutic agents, the application of a single interfering oligonucleotide has not resolved hitherto the required progress in the issue of non-specific binding of antisense oligonucleotides to inadvertent mRNA molecules (Summerton et al., 2007).

The current state of the art hence still faces the fundamental challenge that is the specificity and selectivity of the therapeutic effect exclusively towards the primary target. A real progress in anticancer strategies thus does not lie in the development of new therapeutic agents per se, but in the development of systems that allow selective therapeutic action.

The limitation in terms of insufficient specificity and selectivity of anticancer strategies is solved by the present invention that represents a universal solution for any therapeutic strategy that is based on interference with nucleic acids. The principle of specific and selective recognition of a target nucleic acid together with the principle of selective action is described and explained via targeted interference with causal fusion genes, directly implementing the present invention into anticancer antisense strategies.

In all of the referred patents and publications the term "specificity" strictly refers to the complementary base pairing of the oligonucleotide and target sequence of nucleic acid, i.e. specificity=complementarity; whereas in the present invention the term "specificity" refers to complementary recognition and binding to only one defined target nucleic acid, i.e. specificity=selective recognition of the target nucleic acid.

The present invention is hence clearly distinct from the existing antisense systems designed for controlled intervention of nucleic acids. In other words, the present invention represents a principally innovative solution.

BRIEF SUMMARY OF THE INVENTION

The insufficient specificity stemming from sequence homology to the target nucleic acid, e.g. target mRNA, is effectively addressed by altering of functional state of the target mRNA enabling its selective and specific recognition and subsequent selective intervention, manipulation, detection, quantification, labeling, pre-targeting and sorting, wherein the mRNA is being targeted by a construct comprising at least two sequence-specific oligonucleotides that are mutually interconnected through a size-specific polymeric moiety the length of which defines their mutual distance, wherein each of the sequence-specific oligonucleotides targets a pre-defined target sequence of the mRNA resulting in a stable heteroduplex and through this alteration this mRNA is selectively and specifically recognized. The specific and selective recognition of nucleic acid subsequently can be used for selective therapeutic intervention when the transfer of genetic information coded by the nucleic acid is interrupted, or for diagnostic and research purposes.

By this alternation, defined sequences of nucleic acids are specifically recognized, wherein these sequences have to be at a precisely defined distance from each other. In the case of simultaneous recognition of defined sequences at defined distance from each other, the interfering system designed for the particular spatial distribution of target sequences forms a thermodynamically preferred and energetically stable bond with the target nucleic acid. This principle of recognition minimizes the probability of non-specific interaction and stable binding to inadvertent nucleic acids and hence unwanted interference with nucleic acids outside the primary target is dramatically decreased.

The described principle of nucleic acid recognition dramatically increases the specificity and selectivity of interference with one single, particular selected defined nucleic acid. The described principle is fully universal and it is not restricted only to a mutual interconnection of two sequence-specific oligonucleotides, i.e. it enables purposeful interconnection of any number of oligonucleotides (n≥2) through a corresponding number of non-interfering polymeric linking moieties (n≥1), all with respect to the final application intention.

In a preferred embodiment of the invention, when the target mRNA is a fusion mRNA, each of the specified sequences is located on the respective fusion partner and the interfering system is targeted exclusively towards the fusion nucleic acid that directly ensures selective therapeutic action solely in tumor cells. Moreover, since the antisense systems are able to have an effect in all cells comprising the target mRNA, the present invention brings the prospect of curative therapy, since its implementation allows selective therapeutic targeting of tumor stem cells. By the other words the described innovation brings the hope for full and permanent curing of the oncological disorder.

In the context of anticancer antisense strategies directed to intervention of fusion genes, this principle enables stable interference with the targeted fusion mRNA solely only in the case, when both of the complementary sequences of the individual fusion partners, which furthermore are at a precisely defined distance from each other, are recognized. By this means the specificity and selectivity of interference is significantly increased, whilst the probability of non-specific stable interaction with partially homologous sequences is excluded. In the absence of simultaneous recognition of both of the complementary sequences, i.e. in the case of unwanted interaction with inadvertent mRNA, partial interaction of such system with the non-targeted mRNA is energetically unstable and results in spontaneous disconnection (Dias, Stein, 2002).

The application of the present invention in medicine is demonstrated via antisense systems designed for anticancer therapy with the primary aim of selective intervention of causal fusion genes. In the context of oncological diseases characterized by the presence of fusion genes it means selective targeting exclusively of impaired cells that maximizes therapeutic intervention in the primary target by a fully revolutionary manner. In the field of oncology the present invention represents a revolutionary tool for intervening exclusively tumor cells (i.e. without intervention in healthy cells).

DETAILED DESCRIPTION OF THE INVENTION

The present solution that is the method of altering the functional state of any mRNA enabling its selective and specific recognition and subsequent selective intervention, manipulation, detection, quantification, labeling, pre-targeting and sorting of this mRNA, is proposed to increase the specificity and selectivity of targeting of a particular nucleic acid, and altogether with the specified application field (e.g. controlled inhibition of causal fusion genes; detection of presence and quantification of nucleic acids; nucleic acid labeling; pre-targeting and sorting of nucleic acids) forms integral and inseparable parts of the invention, by which the subject of invention is clearly defined. The subject matter of the invention thus involves specific and selective targeting of any particular nucleic acid through simultaneous recognition of its two (or more) specified sequences, which moreover have to be at a pre-defined particular distance from each other.

From the view of the innovativeness, the present invention provides a revolutionary tool increasing the selectivity and specificity of target nucleic acid recognition allowing its selective intervention, manipulation, detection, quantification, labeling, pre-targeting and sorting.

Selective recognition of a particular nucleic acid (preferably mRNA) in the described way can be subsequently utilized for selective therapeutic intervention of its natural biological function, when alteration of its functional state prevents the transfer of encoded genetic information. In this way the mechanism of the transfer of genetic information from nucleic acid to protein is interrupted, which in the case of fusion mRNA enables direct suppression of the expression of causal fusion oncoproteins.

Analogously, selective recognition of a particular nucleic acid (preferably mRNA) in the described way resulting in alteration of its functional state can be subsequently used for various diagnostic or research purposes:

for a direct detection, visualization, localization and quantification of the recognized nucleic acid (preferably mRNA) via purposeful incorporation of detectable moieties, e.g. FITC, RITC, isotope $P^{32}$ into the primary structure of the sequence-specific oligonucleotides. The use of labeled sequence-specific oligonucleotides enables quantification of the recognized mRNA in the analyzed sample in situ, in vitro, in vivo and ex-vivo, for purification and sorting of the recognized mRNA from other nucleic acids present in the processed sample, for functional analysis of the particular genes via purposeful incorporation of photo-labile functional groups into the primary structure of the sequence-specific oligonucleotides enabling reversible alteration of the functional state of the recognized mRNA.

Terms and Definitions

Antisense system. Unlike the currently used antisense systems for controlled suppression of target mRNAs (Guo et al., 2013; Burnett, Rossi, 2012; Vaishnaw et al., 2010; Missalidis, 2008; Wang et al., 2003; Clark, 2000), the present invention eliminates their most significant limitation which is the insufficient specificity and selectivity of primary target recognition (i.e. promiscuity of antisense oligonucleotides). The promiscuity of standard antisense systems that is closely linked with the length of the antisense oligonucleotide is effectively solved by simultaneous interference of two (or more) antisense oligonucleotides, complementarily recognizing the target sequences localized at a precisely defined distance from each other. In the field of anticancer therapies and especially for controlled suppression of causal fusion genes, the present invention, via its design and mechanism of target mRNA recognition, represents a pilot (hitherto not applied) antisense system.

Construct. The described construct comprises two (or more) sequence-specific oligonucleotides which are mutually interconnected through a size-specific polymeric linking moiety.

Sequence-specific oligonucleotide. Oligonucleotides represents sequences which is complementary to the target nucleic acid (preferably mRNA) or to nucleic acid derivatives. Target nucleic acids are preferably of human origin.

Oligonucleotides may be formed by any nucleotides, optionally by chemical derivatives/analogues such as DNA, RNA, 2'-O-(2-methoxyethyl)-RNA, 2'-O-methyl-RNA, 2'-O-fluoro-RNA, LNA, PNA, morpholino, INA, FANA, ANA, UNA, HNA, etc., and within the present invention they may be mutually combined either as blocks of oligonucleotides with a specific chemical modification or as individual oligonucleotides comprising differently modified nucleotides. Both the nucleobases and the sugar-phosphate backbone may be chemically modified.

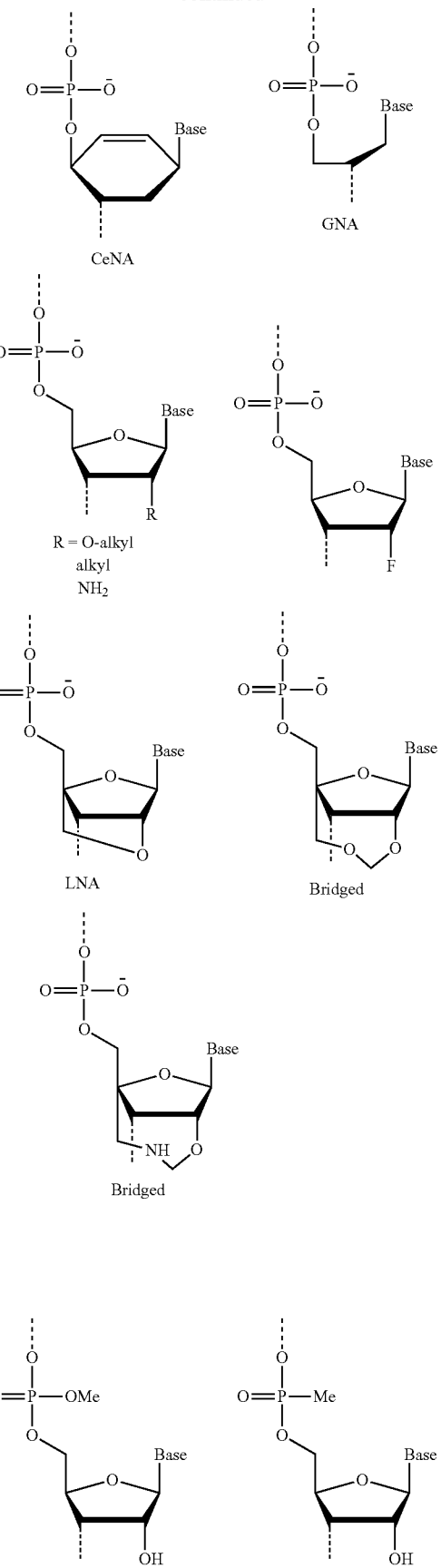

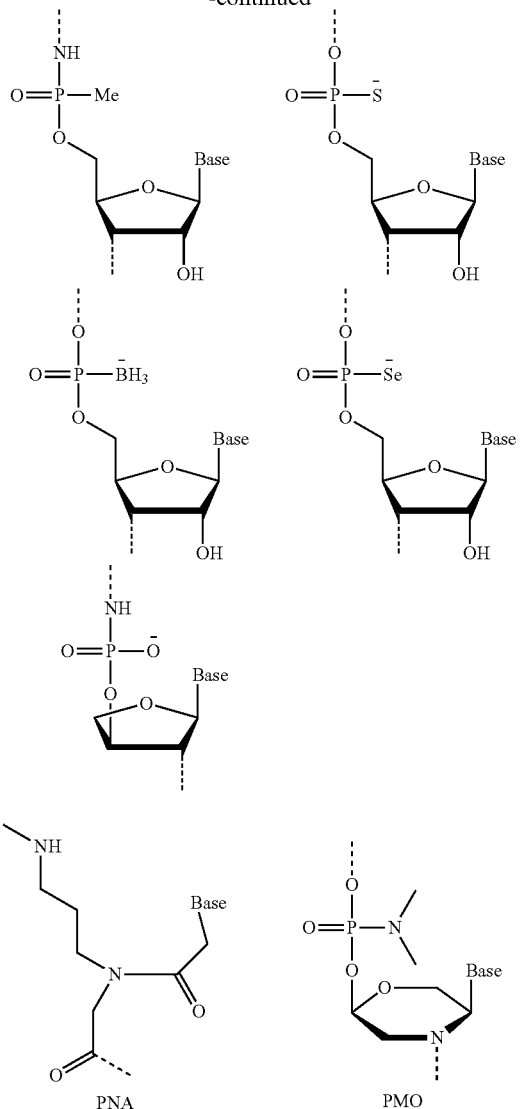

Examples of RNA Derivatives

A: modifications of the sugar moiety; B: modifications of the phosphate bond; C: modifications of the sugar-phosphate backbone.

In the present invention the first oligonucleotide, second oligonucleotide, optionally other oligonucleotide comprise a contiguous sequence of at least 3 nucleotides that is capable of base pairing to the complementary sequence of target nucleic acid (preferably mRNA), wherein
nucleotides may be A, I, U, T, C, G or derivatives thereof
oligonucleotides may comprise any mutual combination of nucleotides or derivatives thereof.

Other preferred sequences of oligonucleotides are at least 4 nucleotides, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, no more than 30, no more than 29, no more than 28, no more than 27, no more than 26, no more than 25, no more than 24, no more than 23, no more than 22, no more than 21, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3 nucleotides long.

The preferred length of the oligonucleotides (individually) is between 10 and 25 nucleotides.

Each of the oligonucleotides within one construct recognizes different complementary sequences of any but single defined target nucleic acid (preferably mRNA).

The length of oligonucleotides within one present construct may vary with respect to the particular application. A stronger interaction with the target nucleic acid may be achieved by a prolongation of the oligonucleotide length. On the other hand, prolongation of the oligonucleotides may impair their bioavailability and cellular internalization. However, since the present invention comprises two (or more) oligonucleotides in combination (cooperative simultaneous binding to the target nucleic acid), it is possible to use shorter oligonucleotides, preferably consisting of less than 17 nucleotides.

Size-specific polymeric linking moiety. The sequence-specific oligonucleotides are mutually interconnected via a size-specific polymeric linking moiety through covalent bond, maintaining the 5' to 3' orientation of all the consecutively interconnected oligonucleotides. The polymeric linking moiety is attached to the 5' end of first oligonucleotide and the 3' end of second oligonucleotide, wherein the oligonucleotides are linked by said polymeric linking moiety.

The polymeric linking moiety may consist of any sequence and number of nucleotides (or nucleotide derivatives/analogues), preferably between 3 and 50 nucleotides (in any of their combination). As well as the polymeric linking moiety may consist of abasic units, in which case the linking moiety is just a sugar-phosphate or chemically modified backbone.

The polymeric linking moiety may be covalently attached to the nucleobase or to the sugar-phosphate backbone of the oligonucleotides.

The polymeric linking moiety may e.g. be a polypeptide, polysaccharide, saturated or unsaturated hydrocarbon (C2-C40), preferably a water soluble natural or synthetic polymer though.

In a preferred embodiment, the polymeric linking moiety comprise a non-nucleotide polymer such as poly(meth)acrylate or modified poly(meth)acrylate (preferably poly (ethyleneoxy) and 2(N,N-dimethylamino)ethyl (meth)acrylate), poly(vinylalcohol), poly(vinylpyrrolidone), poly (ethylene glycol), poly(acrylamide), poly(oxazoline), poly (ethyleneimine), poly(alkyleneoxide), lactone-based polymer, poly(acrylic acid), poly(lactide acid), poly(glycolic acid), poly(propylene), poly(styrene), poly(olefin), poly (amide), poly(cyanoacrylate), poly(imide), poly(ethylene terephtalate), poly(tetramethylene glycol), poly(urethane), as well as a mutual combination thereof or combination of other natural or synthetic polymers (Kadajji, Betageri, 2011).

The length of the polymeric linking moiety may be adjusted according to the specific application of the construct. The length of the polymeric linking moiety is preferably adjusted to the mutual distance between the target sequences of the target nucleic acid, preferably an mRNA. In case that the complementary sequences are up to 20 nucleotides far from each other, the final length of the size-specific polymeric linking moiety may be between 10-100 angstrom based on the distance between nucleotides in a linear, fully extended nucleic acid. The length of the polymeric linking moiety is not restricted and may be freely adjusted according to the final application. It is generally preferred that the polymeric linking moiety is no more than 1000 angstrom in length, no more as 900, 800, 700, 600, 500, 400, 300, 200 or 100 angstrom in length. It is also preferred that the polymeric linking moiety is at least 5 angstrom in length, such as 10, 15, 20, 25, 30, 35, 40 or 45 angstrom in length.

Preferred ranges of the size-specific polymeric linking moiety are between 5 and 1000 angstrom, between 10 and 800 angstrom, between 20 and 500 angstrom, between 20 and 200 angstrom, between 10 and 1000 angstrom and between 20 and 80 angstrom.

Synthesis

Sequence-specific oligonucleotides. The chemical synthesis of sequence-specific oligonucleotides is carried out on a solid support using the phosphoroamidite method, i.e. via consecutive oligomerization of individual monomers derived from protected 2'-deoxynucleosides (dA, dC, dG, dT), ribonucleosides (A, C, G, U) or other chemically modified nucleosides, while both their particular selection and sequence order depend on the final application. The synthetic cycle involves step-wise conjugation of individual nucleosides to the growing oligomer in the order corresponding to the sequence complementary to the target nucleic acid (preferably mRNA). When completed, the sequence-specific oligonucleotide is released from the solid support to the solution, prepared for conjugation with the size-specific linking moiety.

Synthesis of RNA, DNA Oligonucleotides

Synthesis cycle. The synthesis of size-specific oligonucleotides proceeds step-wise in the 3' to 5' direction when one nucleotide is added to the growing oligomer per synthesis cycle until the desired sequence is obtained (Greco, Tor, 2007).

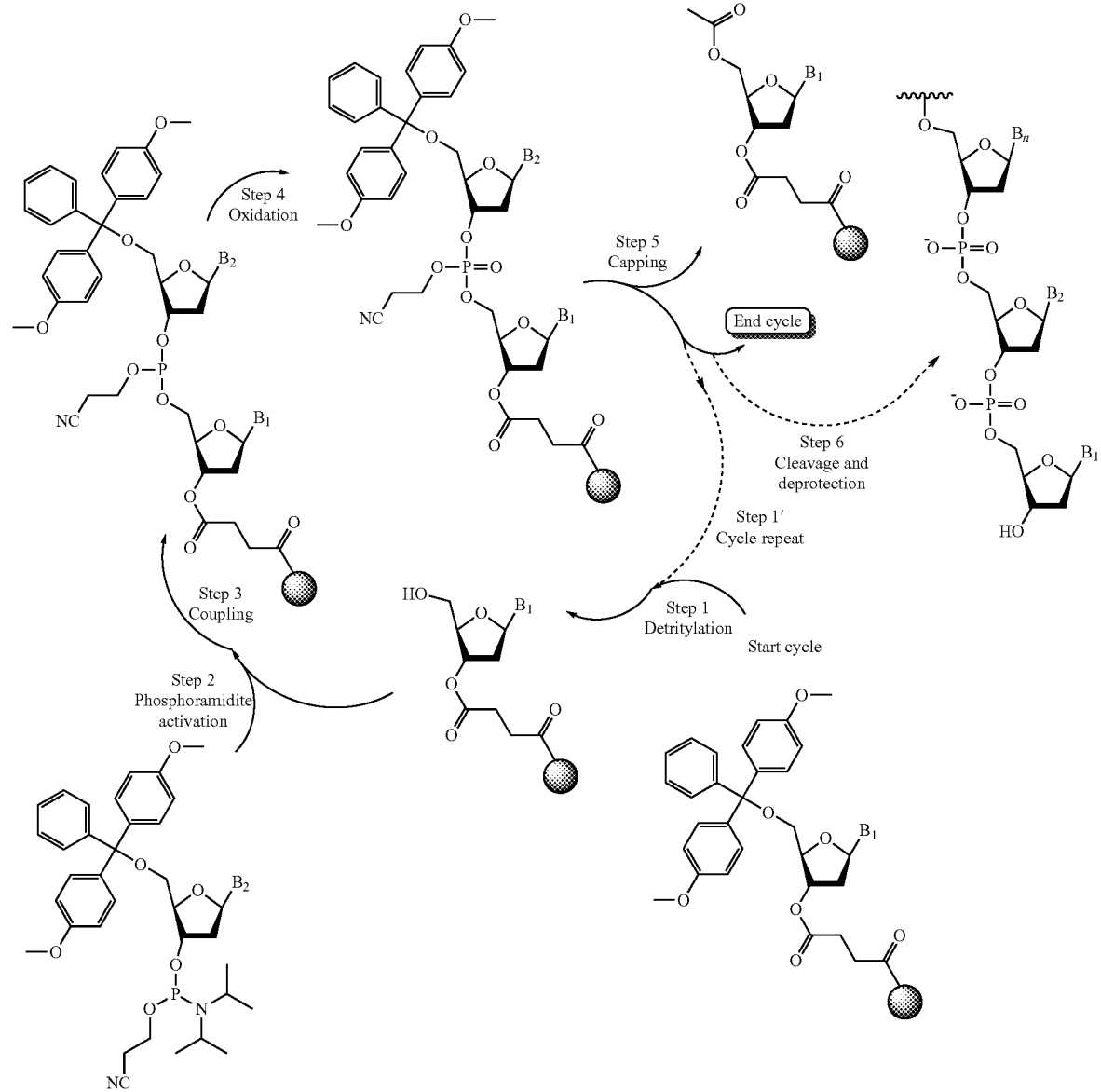

Step 1: De-Tritylation (Removal of Protecting Group)

The dimethoxytrityl (DMT) protecting group is removed by a solution of an acid, e.g. 2% trichloroacetic acid or 3% dichloroacetic acid, in an inert solvent (dichloromethane or toluene).

Step 2 and 3: Activation and Coupling (Conjugation of Nucleosides)

0.02-0.2M solution of nucleoside phosphoramidite in acetonitrile is activated by 0.2-0.7M solution of an acidic azole catalyst i.e. 1H-tetrazole, 2-ethylthiotetrazole, 2-benzylthiotetrazole, 4,5-dicyanoimidazole, or other similar compounds (Wei, 2013). The activated phosphoramidite in 1.5-2.0-fold excess over the support-bound oligonucleotides is then reacted with the starting solid support (first coupling) or a support-bound oligonucleotide precursor (following couplings). The 5'-hydroxy group reacts with the activated phosphoramidite moiety of the incoming nucleoside phosphoramidite to form a phosphite triester linkage. Upon the completion of the coupling reactions, any unbound reagents and by-products are removed by washing.

Step 4: Oxidation

The newly formed tri-coordinated phosphite triester linkages are subsequently oxidized with iodine and water in the presence of weak bases (pyridine, lutidine, or collidine) into a tetra-coordinated phosphate triester. Oxidation may be carried out under anhydrous conditions using tert-butyl hydroperoxide (Alul et al., 1991), or eventually using (1S)-(+)-(10-camphorsulfonyl)-oxaziridine (Manoharan et al., 2000).

Step 5: Capping

The solid support-bound material is treated with a mixture of acetic anhydride and 1-methylimidazole. After termination of the coupling and oxidation reaction, a small proportion of the solid support-bound 5'-OH groups (0.1 to 1%) remains unreacted and needs to be permanently blocked, e.g. by acetylation, in order to prevent the formation of oligonucleotides with an internal base deletion commonly referred to as (n−1) shortmers.

Step 6: Cleavage

Cleavage of the oligonucleotide from the solid support and de-protection is carried out using concentrated ammonium hydroxide.

Synthesis of RNA, DNA Oligonucleotides with Phosphorothioate Backbone

Modified oligonucleotides, wherein one of the oxygen atoms in the phosphodiester backbone is replaced with a sulfur atom, are synthesized analogously to common RNA and DNA oligonucleotides (for details see the Synthesis cycle section). The difference lies in the replacement of the oxidation step with sulphurization.

Synthesis of LNA Oligonucleotides

Modified oligonucleotides, in which the ribose is modified by a covalent bridge between the 2'-O and 4'-C atoms, are synthesized according to Obika et al. (1997) and Koshkin et al. (1998).

Synthesis of PNA Oligonucleotides

Modified oligonucleotides, in which the sugar-phosphate backbone is formed by repeating N-(2-aminoethyl)-glycine units mutually linked via a peptide-like bond, are synthesized according to Nielsen et al. (1991).

Synthesis of Morpholino Oligonucleotides

Modified oligonucleotides, in which the nucleobase is linked to a morpholine ring and interconnected via a phosphorodiamidate linkage, are synthesized according to Summerton and Weller (1991, 1993b, 1997).

Synthesis of GNA Oligonucleotides

Modified oligonucleotides, in which the sugar-phosphate backbone is constituted by repeating glycol moieties interconnected via a phosphodiester linkage, are synthesized according to Ueda et al. (1971) and Cook et al. (1995, 1999).

Synthesis of TNA Oligonucleotides

Modified oligonucleotides, in which the sugar-phosphate backbone is constituted by threose instead of ribose, are synthesized according to Chaput and Szostak (2003).

Size-specific polymeric linking moiety. Chemical synthesis of the size-specific linking moiety is performed using the common methods of organic and polymer chemistry, which allow to control the final molecular weight and hence the final length of the polymer chain, e.g. atom transfer radical polymerization (Matyjaszewski, Xia, 2001). The size-specific polymeric linking moiety may be a bifunctional moiety (i.e. functionally modified at both of its ends) to enable subsequent attachment to both of the sequence-specific oligonucleotides into a final, 5' to 3' oriented construct.

The bifunctional size-specific polymeric linking moiety is preferably formed by non-nucleotide polymers such as polyethylene glycol (PEG), however, the resulting construct is not restricted to this particular type of polymeric moiety (for a detailed description of possible structural variants see the Detailed description of the Invention section). PEGylation of nucleotides and the methods of preparation of PEGylated nucleotides have been described previously by Jäschke et al. (1994) and Fischer et al. (2008).

Alternatively, if the size-specified polymeric linking moiety is not directly synthetized, it is possible to use a commercially available polymer moieties such as 17-O-DMT-hexaethyleneoxide-1-O-phosphoramidite, 8-DMT-O-triethyleneoxide-1-O-phosphoramidite, 6-DMT-hexane diol-1-O-DMT-phosphoramidite, or 1,3-propanediol, phosphoramidite and others.

Construct. The synthesis of the final construct is carried out by consecutive conjugation of the size-specific polymeric linking moiety with the first sequence-specific oligonucleotide and subsequent attaching the resulting precursor to the second sequence-specific oligonucleotide, e.g. via "click" chemistry (Presolski et al., 2011; Besanceney-webler et al., 2011; Bowman, Hoyle, 2010).

EXAMPLES

Figure 1:
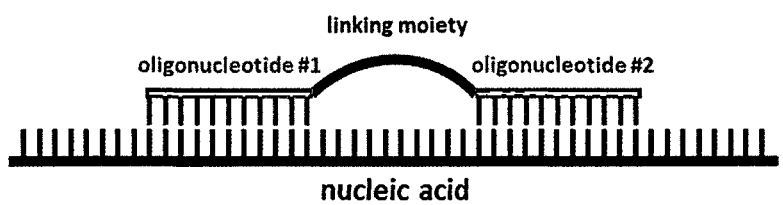
FIG. 1 depicts the general principle of highly specific interaction of the interfering system with the target sequence of the nucleic acid via two sequence-specific oligonucleotides being mutually interconnected through a size-specific linking moiety. The proposed principle is universal and adjustable so that it enables purposeful interconnection of any number of sequence-specific oligonucleotides (n≥2) via a corresponding number of non-interfering size-specific linking moieties (n≥1).
Figure 2:
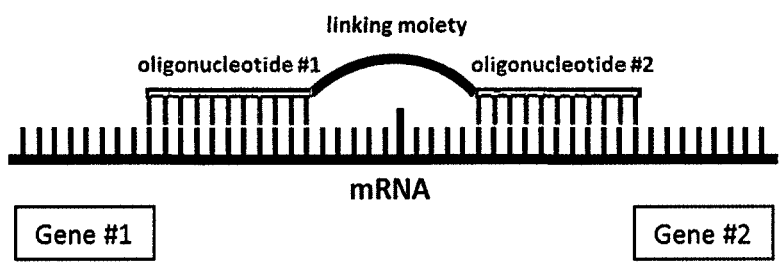
FIG. 2 depicts the highly specific interaction of the interfering system with the target sequences of fusion mRNA via two sequence-specific oligonucleotides mutually interconnected through a size-specific linking moiety. Each of the sequence-specific oligonucleotides binds to the corresponding sequence of the fusion partners.

The solution described in this invention can be considered as universally applicable for selective and specific recognition of any target nucleic acid, preferably fusion mRNA. In the context of antisense systems, when the target nucleic acid is a fusion mRNA (its presence unequivocally characterizes and distinguishes tumor cells from healthy ones), the present invention enables selective recognition and targeting solely of the tumor cells. The innovation in the form of enhanced selectivity and specificity of recognition solely of the target nucleic acid, preferably a fusion mRNA, allows controlled intervention of target fusion genes.

Example 1. Selective and specific recognition of the BCR-ABL fusion mRNA in chronic myelogenous leukemia or Ph+ acute lymphoblastic leukemia, or other neoplasia where BCR-ABL fusion mRNA is present, using the present invention.

The proposed construct selectively and specifically recognizes the BCR-ABL mRNA in a way when the first sequence-specific oligonucleotide targets the sequence of BCR and the second oligonucleotide targets the sequence of ABL, whilst both of the oligonucleotides are mutually interconnected through a size-specific polymeric linking moiety. It is also possible to apply more than two sequence-specific oligonucleotides, when each of them targets either the BCR or ABL, wherein each of the fusion partners is targeted by at least one oligonucleotide. The sequence-specific oligonucleotides are mutually interconnected through a corresponding number of polymeric linking moieties. A stable, thermodynamically and energetically preferable complementary interaction between the construct and the targeted BCR-ABL mRNA is formed only in the case, when each of the target sequences is fully recognized and moreover spaced from each other by a certain distance defined by the size-specific polymeric linking moiety. By this means the probability of stable binding of the construct to partially homologous mRNAs is minimized that prevents a stable intervention with inadvertent mRNA molecules. With respect to the fact, that fusion BCR-ABL mRNA is exclusively present in tumor cells, the described principle of BCR-ABL mRNA recognition results in preferential and stable intervention solely in tumor cells, thereby to a selective recognition and targeting of tumor cells. The sequences of individual sequence-specific oligonucleotides within the construct are complementary to the target sequences of individual fusion partners BCR, ABL. The target sequences of BCR, ABL may be optional referring to the primary sequence of the fusion BCR-ABL mRNA, however in a preferred embodiment the distance of the target sequences from the fusion breakpoint site is no more than 100 nucleotides, irrespective of the particular fusion BCR-ABL mRNA variant.

```
                                               (SEQ ID NO: 1)
5' acguucc ugaucuccuc ugacuaugag cgugcagagu ggagggagaa cauccgggag cagcagaaga aguguuucag aagcuuccc cugacauccg uggagcugca gaugcugacc aacucgugug ugaaacucca gacuguccac agcauuccgc ugaccaucaa uaaggaagaa gcccuucagc ggccaguagc aucuaacuuu gagccucagg guaugaauga agccgcucau uggaacucca aagaaaaccu ucucgcugga cccagugaaa augaccccaa ccuuuucguu gcacuguaug auuuugugc caguggagau aacacucuaa gcauaacuaa aggugaaag
```

Partial primary sequence of fusion BCR ABL mRNA (GenBank: AJ311467.1); BCR—black, ABL—grey; target sequences are underlined.

```
                      linking moiety (8 nt gap)
      3' CTGGTAGTTATTCCTTC ---------------- GTCGCCGGTCATCGTAG 5'
             (SEQ ID NO: 8)                      (SEQ ID NO: 9)
```

Example of the construct designed for selective and specific recognition of BCR ABL mRNA. The complementary oligonucleotide to BCR (17 nt) and ABL1 (17 nt) are shown in black and grey, respectively.

Analogously to Example 1, Examples 2-7 in an abridged form as well as the list of other fusion mRNAs are given below.

Example 2. Selective and specific recognition of the AML1-ETO fusion mRNA in acute myeloid leukemia M2 or other neoplasia where AML1-ETO fusion mRNA is present, using the present invention.

```
                                               (SEQ ID NO: 2)
5' aucaaaa ucacagugga ugggccccga gaaccucgaa aucguacuga gaagcacucc acaaugccag acucaccugu ggaugugaag acgcaaucua ggcugacucc uccaacaaug ccaccucccc caacuacuca aggagcucca agaaccaguu cauuuacacc gacaacguua acuaauggca cgagccauuc uccuacagcc uugaauggcg cccccucacc acccaauggc
```

Partial primary sequence of fusion AML1-ETO mRNA (GenBank: S78158.1); AML1—black, ETO—grey; target sequences are underlined.

```
              linking moiety (17 nt gap)
3' TAGTGTCACCTACCCG ---------------- GCATGACTCTTCGTGAGG 5'
    (SEQ ID NO: 10)                    (SEQ ID NO: 11)
```

Example of the construct designed for selective and specific recognition of AML1-ETO mRNA. The complementary oligonucleotide to AML1 (16 nt) and ETO (18 nt) are shown in black and grey, respectively.

Example 3. Selective and specific recognition of the CBFB-MY H11 fusion mRNA in acute myeloid leukemia M4 or other neoplasia where CBFB-MY H11 fusion mRNA is present, using the present invention.

```
                                    (SEQ ID NO: 3)
5' uuugaag auagagacag gucucaucgg gaggaaaugg agaaugaagu ugagagcguc acagggaugc uuaacgaggc cgaggggaag gccauuaagc uggccaagga cguggcgucc cucaguuccc agcuccagga cacccaggag uu
```

Partial primary sequence of fusion CBFB-MY H11 mRNA (GenBank: AF249897.1); CBFB—black, MYH11—grey; target sequences are underlined.

```
              linking moiety (12 nt gap)
3' TATCTCTGTCCAGAGTAGCC ---------------- TTACTTCAACTCTCG 5'
      (SEQ ID NO: 12)                      (SEQ ID NO: 13)
```

Example of the construct designed for selective and specific recognition of CBFB-MYH11 mRNA. The complementary oligonucleotide to CBFB (20 nt) and MYH11 (15 nt) are shown in black and grey, respectively.

Example 4. Selective and specific recognition of the RBM15-MKL1 fusion mRNA in acute myeloid leukemia or other neoplasia where RBM15-MKL1 fusion mRNA is present, using the present invention.

```
                                    (SEQ ID NO: 4)
5' ucccugu gggggcaac aaagacaagg aaaacaccgg gguccuucau gccuucccac cuugugaguu cucccagcag uuccuggauu ccccugccaa ggcacuggcc aaaucugaag aagauuaccu ggucaugauc auuguccgug cuuugaaaag uccagccgca uuucaugagc agagaaggag cuuggagcqg gccaagacag aggacuaucu caaacggaag auucguuccc gaccggagag aucagagcug gucagaaugc acauuuugga agagaccucg gcugagccau
```

Partial primary sequence of fusion RBM15-MKL1 mRNA (GenBank: AF364035.1); RBM15—black, MKL1—grey; target sequences are underlined.

```
       linking moiety (8 nt gap)      linking moiety (12 nt gap)
3' CGGTTTAGACTTCT --------- ACCAGTACTAGTAACAG --------- TCAGGTCGGCGTAAAG 5'
    (SEQ ID NO: 14)           (SEQ ID NO: 15)              (SEQ ID NO: 16)
```

Example of the construct designed for selective and specific recognition of RBM15-MKL1 mRNA. The complementary oligonucleotide to RBM15 (14 nt, 17 nt) and MKL1 (17 nt) are shown in black and grey, respectively.

Example 5. Selective and specific recognition of the MOZ-CBP fusion mRNA in acute myeloid leukemia or other neoplasia where MOZ-CBP fusion mRNA is present, using the present invention.

(SEQ ID NO: 5)
5' aaaugaa cuu uucccua gagaauacuu ccgucguuug ucuucgcagg auguacucag gugucagucc ucuucuaaga ggaagucuaa agaugaagaa gaag<u>augaag agucagauga</u>

<u>ug</u>cugaugau gggaaua<u>acu gggaacacaa guccau</u>uugg acagcccuu<u>u agucaagcug gagg</u>gcagcc aaugggagcc acuggaguga accccaguu agccagcaaa cagagcaugg ucaacaguuu gcccaccuuc ccuacagaua ucaagaauac uucagucacc aacgugccaa Partial primary sequence of fusion MOZ-CBP mRNA (GenBank: AJ251844.1); MOZ—black, CBP—grey; target sequences are underlined.

```
           linking moiety (15 nt gap)    linking moiety (13 nt gap)
3' TACTTCTCAGTCTACTAC ------ TGACCCTTGTGTTCAGGTA ------ ATCAGTTCGACCTCC 5'
      (SEQ ID NO: 17)          (SEQ ID NO: 18)          (SEQ ID NO: 19)
```

Example of the construct designed for selective and specific recognition of MOZ-CBP mRNA. The complementary oligonucleotide to MOZ (18 nt, 19 nt) and CBP (15 nt) are shown in black and grey, respectively.

Example 6. Selective and specific recognition of the TAF2N-TEC fusion mRNA in myxoid chondrosarcoma or other neoplasia where TAF2N-TEC fusion mRNA is present, using the present invention.

(SEQ ID NO: 6)
5' uuaugau cagcagcaug auuccuauag ucaaaaccag caguccuauc auucacaaag ggaaaacuac <u>agccaccaca</u>

<u>cacaag</u>auau gcccu<u>gcauc caagcccaau au</u>agcccuuc cccuc<u>caggu uccaguuaug c</u>ggcgcagac auacagcucg gaauacacca cggagaucau gaaccccgac uacaccaagc ugaccaugga ccuuggcagc acugagauca cgg cuacagc Partial primary sequence of fusion TAF2N-TEC mRNA (GenBank: AJ245932.1); TAF2N—black, TEC—grey; target sequences are underlined.

```
          linking moiety (9 nt gap)   linking moiety (13 nt gap)
3' TCGGTGGTGTGTGTTC ------ CGCAGGTTCGGGTTATA ------ GTCCAAGGTCAATACG 5'
      (SEQ ID NO: 20)           (SEQ ID NO: 21)          (SEQ ID NO: 22)
```

Example of the construct designed for selective and specific recognition of TAF2N-TEC mRNA. The complementary oligonucleotides to TAF2N (16 nt) and TEC (17 nt, 16 nt) are shown in black and grey, respectively.

Example 7. Selective and specific recognition of the BRD4-NUT fusion mRNA in mediastinal carcinoma or other neoplasia where BRD4-NUT fusion mRNA is present, using the present invention.

(SEQ ID NO: 7)
5' gagcgcu augucaccuc cuguuugcgg aagaaaagga aaccucaagc ugagaaaguu gaugugauug ccggcuccuc caagaugaag ggcuucucgu ccucagaguc <u>ggagagcucc</u>

<u>agugagucca</u> gcuccuc<u>uga cagcgaagac uccga</u>aacag ca<u>ucugcauu gccgggaccg</u> gauaugagca ugaaaccuag ugccgcccug ucuccauccc cugcacuucc cuuucuccca ccaacuucug acccaccaga ccacccaccc agggagccac cuccacagcc caucaugccu Partial primary sequence of fusion BRD4-NUT mRNA (GenBank: AY166680.1); BRD4—black, NUT—grey; target sequences are underlined.

```
         linking moiety (7 nt gap)    linking moiety (7 nt gap)    linking moiety (8 nt gap)
3' TCTCGAGGTCACTCAGGT ---- ACTGTCGCTTCTGAGGCT ---- AGACGTAACGGCCCTGGC ---- GTACTTTGGATCACGGCG 5'
    (SEQ ID NO: 23)          (SEQ ID NO: 24)          (SEQ ID NO: 25)         (SEQ ID NO: 26)
```

Example of the construct designed for selective and specific recognition of BRD4-NUT mRNA. The complementary oligonucleotides to BRD4 (18 nt, 18 nt) and NUT (18 nt, 18 nt) are shown in black and grey, respectively.

In analogy, it is possible to selectively and specifically recognize the following fusion mRNAs:

| | |
|---|---|
| fusion PML-RARA mRNA | fusion BCM-IL2 mRNA |
| fusion TEL-AML1 mRNA | fusion CEV14-PDGFRB mRNA |
| fusion TCR-RBTN2 mRNA | fusion RBM15-MKL mRNA |
| fusion TMP RSS2-ETS mRNA | fusion ETV6-NTRK3 mRNA |
| fusion NPM-ALK mRNA | fusion TFE3-PRCC mRNA |
| fusion PLZF-RARA mRNA | fusion TFE3-ASPSCR1 mRNA |
| fusion MLL-AF9 mRNA | fusion PAX8-PPARG mRNA |
| fusion DEK-CAN mRNA | fusion TET1-TP53 mRNA |
| fusion FUS-ERG mRNA | fusion TFEB-ALPHA mRNA |
| fusion AML1-MTG mRNA | fusion TFE3-PSF mRNA |
| fusion AML1-EAP mRNA | fusion CHOP-EWS mRNA |
| fusion NUP98-PMX1 mRNA | fusion PAX3-FKHR mRNA |
| fusion MLL-AFP1 mRNA | fusion JAZF1-JJAZ1 mRNA |
| fusion EA2-HLF mRNA | fusion FUS-CREB312 mRNA |
| fusion MOZ-P300 mRNA | fusion TMP3-ALK mRNA |
| fusion TEL-PDGFRB mRNA | fusion CLTC-ALK mRNA |
| fusion MLL-AFX1 mRNA | fusion RPN1-EVI1 mRNA |
| fusion E2A-PBX1 mRNA | fusion EWS-FLI1 mRNA |
| fusion MLL-AF6 mRNA | fusion AML1-EVI-1 mRNA |
| fusion NUP98-HOXA9 mRNA | fusion ETV6-MN1 mRNA |
| fusion MLL-AF4 mRNA | fusion MLL-ENL mRNA |
| fusion NUP98-RAP1GDS1 mRNA | fusion CALM-AF10 mRNA |
| fusion FUS-CHOP mRNA | fusion PAX7-FKHR mRNA |
| fusion SYT-SSX mRNA | fusion EWS-CHN mRNA |
| fusion TCF12-TEC mRNA | fusion EWS-WT1 mRNA |
| fusion ASPL-TFE3 mRNA | fusion COL1A1-PDGFB mRNA |
| fusion TPM4-ALK mRNA | |

Other applications of the present invention are demonstrated via Examples 8-11.

Example 8. Selective and specific therapeutic intervention to the natural biological function of any mRNA, when after application of the present invention and alteration of the functional state of the recognized mRNA the transfer of genetic information coded by this mRNA is prevented. Thereby, the mechanism of translation of the genetic information from mRNA to protein is interrupted which in case of a fusion mRNA, such as in Examples 1-7, results in direct suppression of the expression of causal fusion oncoproteins.

Example 9. Selective and specific detection of any mRNAs and subsequent quantification thereof, when sequence-specific oligonucleotides contain an incorporated detectable label, such as FITC, RITC, $P^{32}$ isotope, which after application of the present invention and alteration of the functional state of the recognized mRNA emits a detectable signal corresponding to the stable heteroduplex.

Example 10. Purification and sorting of selectively and specifically recognized mRNA from other nucleic acids present in the analyzed sample, when the application of the present invention results in the alteration of the functional state of the recognized mRNA, i.e. a stable heteroduplex with different electrophoretic mobility is formed. Consequently, it is possible to separate the recognized mRNAs from other nucleic acids by applying of an external electric field. Analogously, via purposeful modification of sequence-specific oligonucleotides with primary antibodies, it is possible to sort the recognized mRNA after application of the present invention on the basis of its interaction with secondary antibodies.

Example 11. Functional analysis of individual genes, when a primary structure of sequence-specific oligonucleotides contain incorporated photo-labile functional groups enabling reversible change of the functional state of recognized mRNA. After application of the present invention and alteration of the functional state of the recognized mRNA it is possible to reverse this effect by application of radiation of a required wavelength. In this way it is possible to selectively and specifically study effects of suppression of gene expression under in situ and in vivo conditions.

The invention claimed is:

1. A method of binding a target nucleic acid wherein the method comprises contacting the target nucleic acid with a construct to form a heteroduplex; and wherein:
the target nucleic acid encodes a fusion protein and comprises first and second fusion partners and first and second target sequences, the first target sequence being completely localized within the first fusion partner, and the second target sequence being completely localized within the second fusion partner;
the construct consists of first and second sequence-specific single-stranded oligonucleotides that are interconnected through a linking moiety;
each of the sequence-specific single-stranded oligonucleotides consists of 10 to 30 nucleotides, the first oligonucleotide is fully complementary to the first target sequence, and the second oligonucleotide is fully complementary to the second target sequence, such that the construct binds to the target nucleic acid to form a heteroduplex;
the linking moiety is from 5 to 200 angstroms in length; and the linking moiety comprises:
a) a sugar-phosphate backbone without a base, a chemically modified sugar-phosphate backbone without a base, or a combination thereof;
b) a polypeptide;
c) a polysaccharide;
d) a non-nucleotide polymer comprising poly(meth)acrylate, modified poly(meth)acrylate, poly(vinyl alcohol), poly(vinylpyrrolidone), poly(ethylene glycol), poly (acrylamide), poly(oxazoline), poly(ethyleneimine), poly(alkyleneoxide), lactone based polymer, poly (acrylic acid), poly(lactic acid), poly(glycolic acid), poly(propylene), poly(styrene), poly(olefin), poly (amide), poly(cyanoacrylate), poly(imide), poly(ethylene terephthalate), poly(tetramethylene glycol), poly (urethane), or a combination thereof; or
e) a combination of any of a) to d).

2. The method of claim 1, wherein the target nucleic acid is an mRNA.

3. The method of claim 1, wherein the first and second target sequences are localized not more than 100 nucleotides from a fusion breakpoint site.

4. The method of claim 2, wherein the length of the linking moiety ranges between 5 and 100 angstroms, between 20 and 200 angstroms, between 10 and 100 angstroms, between 20 and 100 angstroms, or between 20 and 80 angstroms.

5. The method of claim 2, wherein the linking moiety is attached to the 5' end of one sequence-specific single-stranded oligonucleotide and the 3' end of the other sequence-specific single-stranded oligonucleotide.

6. The method of claim 2, wherein the linking moiety is a polymeric linking moiety.

7. The method of claim 1, wherein the modified poly (meth)acrylate comprises poly(ethyleneoxy), 2(N,N-dimethylamino)ethyl (meth)acrylate, or a combination thereof.

8. The method of claim 2, wherein the sequence-specific single-stranded oligonucleotides comprise natural nucleotides, nucleotide derivatives, nucleotide analogs, or a combination of two or more of natural nucleotides, nucleotide derivatives, or nucleotide analogs.

9. The method of claim 8, wherein the natural nucleotides, nucleotide derivatives, nucleotide analogs, or a combination of two or more of natural nucleotides, nucleotide derivatives, or nucleotide analogs are mutually combined either as blocks of oligonucleotides with a specific chemical modification or as individual oligonucleotides consisting of differently modified nucleotides.

10. The method of claim 8, wherein the sequence-specific single-stranded oligonucleotides independently comprise DNA, RNA, 2'-O-(2-methoxyethyl)-RNA, 2'-O-methyl-RNA, 2'-fluoro-RNA, LNA, PNA, morpholino, INA, FANA, ANA, UNA, HNA, or a combination thereof.

11. The method of claim 8, wherein the sequence specific single-stranded oligonucleotides consist of 10 to 25 nucleotides.

12. The method of claim 1, wherein the length of the linking moiety corresponds to a number of nucleotides separating the target sequences to enable binding of the sequence-specific single-stranded oligonucleotides to the target sequences and the formation of the heteroduplex.

13. The method of claim 1, wherein the method is an in vitro method or an ex vivo method.

14. A construct for binding a target nucleic acid, wherein:
the target nucleic acid encodes a fusion protein and comprises first and second fusion partners and first and second target sequences, the first target sequence being completely localized within the first fusion partner, and the second target sequence being completely localized within the second fusion partner;
the construct consists of first and second sequence-specific single-stranded oligonucleotides that are interconnected through a linking moiety;
each of the sequence-specific single-stranded oligonucleotides consists of 10 to 30 nucleotides, the first oligonucleotide is fully complementary to the first target sequence, and the second oligonucleotide is fully complementary to the second target sequence, such that the construct binds to the target nucleic acid to form a heteroduplex;
the linking moiety is from 5 to 200 angstroms in length; and the linking moiety comprises:
a) a sugar-phosphate backbone without a base, a chemically modified sugar-phosphate backbone without a base, or a combination thereof;

b) a polypeptide;
c) a polysaccharide;
d) a non-nucleotide polymer comprising poly(meth)acrylate, modified poly(meth)acrylate, poly(vinyl alcohol), poly(vinylpyrrolidone), poly(ethylene glycol), poly(acrylamide), poly(oxazoline), poly(ethyleneimine), poly(alkyleneoxide), lactone based polymer, poly(acrylic acid), poly(lactic acid), poly(glycolic acid), poly(propylene), poly(styrene), poly(olefin), poly(amide), poly(cyanoacrylate), poly(imide), poly(ethylene terephthalate), poly(tetramethylene glycol), poly(urethane), or a combination thereof; or
e) a combination of any of a) to d).

15. A composition comprising the construct of claim 14.

16. A pharmaceutical composition comprising the construct of claim 14.

17. A method of treating a cancer patient, wherein the method comprises administering the pharmaceutical composition of claim 16 to a patient in need thereof, and wherein the patient has a cancer caused by an oncogenic gene fusion and the construct forms a heteroduplex with mRNA expressed from the gene fusion.

18. The method of claim 17, wherein the patient has leukemia.

19. The method of claim 18, wherein the leukemia is chronic myelogenous leukemia, acute myeloid leukemia, or acute lymphoblastic leukemia.

20. A method of killing tumor cells, wherein the method comprises administering the pharmaceutical composition of claim 16 to tumor cells, wherein the tumor cells comprise an oncogenic gene fusion and the construct forms a heteroduplex with mRNA expressed from the gene fusion.

21. The method of claim 20, wherein the tumor cells are in a patient.

22. A method of diagnosing cancer in a patient, wherein the method comprises administering the composition of claim 15 to a biological sample from a patient in need thereof, and detecting formation of the heteroduplex, wherein the formation of the heteroduplex indicates that the patient has cancer.

23. The method of claim 1, wherein the first and second sequence-specific single-stranded oligonucleotides consist of SEQ ID NO: 8 and SEQ ID NO: 9, respectively.

24. The construct of claim 14, wherein the first and second sequence-specific single-stranded oligonucleotides consist of SEQ ID NO: 8 and SEQ ID NO: 9, respectively.

25. The method of claim 1, wherein the first and second sequence-specific single-stranded oligonucleotides consist of SEQ ID NO: 10 and SEQ ID NO: 11, respectively.

26. The method of claim 1, wherein the first and second sequence-specific single-stranded oligonucleotides consist of SEQ ID NO: 12 and SEQ ID NO: 13, respectively.

27. The construct of claim 14, wherein the first and second sequence-specific single-stranded oligonucleotides consist of SEQ ID NO: 10 and SEQ ID NO: 11, respectively.

28. The construct of claim 14, wherein the first and second sequence-specific single-stranded oligonucleotides consist of SEQ ID NO: 12 and SEQ ID NO: 13, respectively.

29. The construct of claim 14, wherein the length of the linking moiety ranges between 5 and 100 angstroms, between 20 and 200 angstroms, between 10 and 100 angstroms, between 20 and 100 angstroms, or between 20 and 80 angstroms.

30. The construct of claim 14, wherein the linking moiety is attached to the 5' end of one sequence-specific single-stranded oligonucleotide and the 3' end of the other sequence-specific single-stranded oligonucleotide.

31. The construct of claim 14, wherein the linking moiety is a polymeric linking moiety.

32. The construct of claim 14, wherein the modified poly(meth)acrylate comprises poly(ethyleneoxy), 2(N,N-dimethylamino)ethyl (meth)acrylate), or a combination thereof.

33. The construct of claim 14, wherein the sequence-specific single-stranded oligonucleotides comprise natural nucleotides, nucleotide derivatives, nucleotide analogs, or a combination of two or more of natural nucleotides, nucleotide derivatives, or nucleotide analogs.

34. The construct of claim 33, wherein the natural nucleotides, nucleotide derivatives, nucleotide analogs, or a combination of two or more of natural nucleotides, nucleotide derivatives, or nucleotide analogs are mutually combined either as blocks of oligonucleotides with a specific chemical modification or as individual oligonucleotides consisting of differently modified nucleotides.

35. The construct of claim 33, wherein the sequence-specific single-stranded oligonucleotides independently comprise DNA, RNA, 2'-O-(2-methoxyethyl)-RNA, 2'-O-methyl-RNA, 2'-fluoro-RNA, LNA, PNA, morpholino, INA, FANA, ANA, UNA, HNA, or a combination thereof.

* * * * *